United States Patent [19]

Schoendorfer

[11] Patent Number: 5,135,667
[45] Date of Patent: Aug. 4, 1992

[54] METHOD AND APPARATUS FOR ADMINISTRATION OF ANTICOAGULANT TO RED CELL SUSPENSION OUTPUT OF A BLOOD SEPARATOR

[75] Inventor: Donald W. Schoendorfer, Santa Ana, Calif.

[73] Assignee: Baxter International Inc., Deerfield, Ill.

[21] Appl. No.: 538,306

[22] Filed: Jun. 14, 1990

[51] Int. Cl.⁵ .................. B01D 36/02; B01D 61/18
[52] U.S. Cl. .................. 210/782; 210/85; 210/143; 210/195.1; 210/206; 210/257.1; 210/257.2; 210/295; 210/297; 210/321.68; 210/335; 210/767; 210/805; 210/806
[58] Field of Search ............ 210/739, 767, 782, 805, 210/85, 96.1, 143, 206, 257.1, 321.67, 321.68, 806, 195.1, 257.2, 295, 297, 335; 604/4-6

[56] References Cited

U.S. PATENT DOCUMENTS

| | | | |
|---|---|---|---|
| 4,605,503 | 8/1986 | Bilstad et al. | 210/651 |
| 4,680,025 | 7/1987 | Kruger et al. | 604/6 |
| 4,708,714 | 11/1987 | Larsson et al. | 604/5 |
| 4,776,964 | 10/1988 | Schoendorfer | 210/782 |
| 4,806,247 | 2/1989 | Schoendorfer et al. | 210/321.68 |
| 4,842,576 | 6/1989 | Lysaght et al. | 604/6 |
| 4,850,998 | 7/1989 | Schoendorfer | 604/28 |
| 4,851,126 | 7/1989 | Schoendorfer | 210/321.67 |
| 4,871,462 | 10/1989 | Fischel et al. | 210/651 |
| 4,897,185 | 1/1990 | Schuyler | 210/90 |
| 5,034,135 | 7/1991 | Fischel | 210/651 |

FOREIGN PATENT DOCUMENTS 0310205 7/1988 European Pat. Off.
WO88/05332 4/1989 PCT Int'l Appl.

Primary Examiner—W. Gary Jones
Attorney, Agent, or Firm—Bradford R. L. Price; Daniel D. Ryan; Paul C. Flattery

[57] ABSTRACT

Method and apparatus for machine separation of blood and blood components that utilizes improved administeration of anticoagulant to the red cell suspension output. Anticoagulant is added to incoming whole blood in an amount sufficient to prevent clotting of the whole blood in the flow path upstream of the blood component separator, but in an amount insufficient to prevent clotting of the red cell suspension created by the separator. Anticoagulant is added to the red cell suspension downstream of the separator in order to prevent clotting. By adding an additional aliquot of anticoagulant to the red cell suspension, the amount of anticoagulant added to whole blood before separation can be reduced or eliminated, resulting in an increase in platelet yield during the blood component separation step.

40 Claims, 7 Drawing Sheets

METHOD AND APPARATUS FOR ADMINISTRATION OF ANTICOAGULANT TO RED CELL SUSPENSION OUTPUT OF A BLOOD SEPARATOR

Filed concurrently herewith is United States Patent Application Ser. No. 538,301, entitled "Automated Blood Compenent Separation Procedure and Apparatus Promoting Different Functional Characteristics in Multiple Blood Components", Yean Yow Hwang et al., inventors, assigned to the assignee of the present invention.

FIELD OF THE INVENTION

The present invention relates generally to automated blood component separation and more particularly relates to promoting different functional characteristics in different blood components, such as increased platelet yield for platelet collection and resistance to clotting in packed red blood cell suspensions.

BACKGROUND OF THE INVENTION

There today exist a number of automated donor hemapheresis systems for the separation of blood, including whole blood, into components or fractions. The systems are designed: to collect one or more components, such as plasma, white cells, platelets and red cells, for further use or for disposal; to return certain components to the donor, who may be a patient; and/or to treat a component, for subsequent return to a donor. One such system is the Autopheresis-C ® system sold by Baxter Healthcare Corporation of Deerfield, Ill., a wholly owned subsidiary of the assignee of the present invention. That system utilizes a microprocessor-controlled instrument including automated processing programs, in conjunction with a disposable set. The Autopheresis-C ® device may, when a disposable plasmapheresis set is installed therein, be used to collect plasma from whole blood drawn from a donor. A rotating membrane in a separation chamber of the disposable may in fact be wetted by an anticoagulant priming operation before blood is withdrawn from the donor, as shown in U.S. patent application Ser. No. 07/106,089, filed Oct. 7, 1987, entitled "Method for Wetting a Plasmapheresis Filter with Anticoagulant", and corresponding PCT International Application Publication No. WO89/03229.

For the collection of platelets and plasma, the Autopheresis-C ® system uses a single, two stage set as disclosed in U.S. Pat. No. 4,851,126, entitled "Apparatus and Methods for Generating Platelet Concentrate". The set may include a rotating membrane separation chamber as set forth in U.S. patent application Ser. No. 73,378 and in corresponding Canadian Patent No. 1,261,765, as well as a centrifuge separator as set forth in U.S. Pat. Nos. 4,776,964 and 4,911,833 entitled "Closed Hemapheresis System and Method" and in International PCT Publication No. W088/05332 entitled "Continuous Centrifugation System and Method for Directly Deriving Intermediate Density Material from a Suspension". If an anticoagulant source is preattached to the set, a biologically closed system, as medically defined, can be created.

The two stage system enables the collection of blood from a donor for separation into platelet-rich plasma and packed red cells. The red cell suspension is returned to the donor by means of the same needle used to withdraw the whole blood. The platelet-rich plasma is collected in a container. The machine and set are disconnected from the donor. The collected platelet-rich plasma is then separated into plasma and platelet concentrate, utilizing the second stage of the biologically closed set.

Another automated closed system for separating blood fractions is the CS-3000 ® cell separator sold by Baxter Healthcare Corporation. Still another system is the Model 50 separator sold by Haemonetics Corp. of Braintree, Mass.

During withdrawal of blood and its subsequent treatment/separation, anticoagulant must be added in order to prevent clotting of the blood within the disposable tubing and separation set during the separation or collection of the blood. The conventional method of administering anticoagulant during automated apheresis procedures is to add anticoagulant during the step of withdrawal of the whole blood from a donor's vein. Anticoagulant from an anticoagulant container is administered through tubing to a location just downstream from the phlebotomy needle at a tubing junction, where the anticoagulant tubing line merges with the unanticoagulated whole blood tubing line, adjacent the phlebotomy needle in the donor.

There are at least four separate reasons for the addition of anticoagulant to the donor's blood during an extracorporeal blood procedure. The first reason is to prevent the blood from clotting as it travels through the various tubes to the blood separator of the disposable set. The second reason is to prevent the blood from clotting as it is being separated. All separators require some exposure of blood to fluid shear stresses and these shear stresses can induce coagulation or agglomeration. The third reason is to prevent the separated cells from coagulation as they are being pumped through reinfusion filters and back to the donor. The fourth reason is to provide enough nutrients and sufficient pH buffering to permit storage of the separated blood component for the required duration of time.

The demand for anticoagulant in each of the four general steps identified above depends on the particular automated apheresis procedure. Some systems may induce significantly more shear stress during blood separation than other systems and therefore the upper limit demand for anticoagulant would be set by the separation step. Also, the separation technology used may have different stages wherein each separation stage may have its own, different demand level for the amount of anticoagulant in the blood. For example, if an intermediate stage separation such as platelet-rich plasma is collected first and then a secondary stage separation is utilized to separate the platelet-rich plasma (PRP) into plasma and platelet concentrate, there may be different requirements for anticoagulant at these two stages.

Alternatively, if the separated blood product is platelets for example and if the requirement is to store the platelets for five days, this relatively lengthy platelet storage period can often require more anticoagulant than any other stage in the blood withdrawal and separation procedure.

The addition of different amounts of anticoagulant to different blood components in manual (non-automated) blood collection is identified in "Platelet Concentrates from Acidified Plasma: A Method of Preparation Without the Use of Additives", Wanda S. Chappell. As best understood, the procedure explained therein utilized different aliquots of anticoagulant in different blood component containers to better optimize the amount of anticoagulant in a collected blood component.

Generally, the prior art has dealt with the issue of anticoagulant demand in automated procedures by adding to the whole blood, almost immediately upon its withdrawal from the donor, enough anticoagulant to meet the highest anticoagulant demand level during the entire withdrawal, separation, return and storage procedure. The anticoagulant is added adjacent the phlebotomy needle. The anticoagulant mixes with the whole blood upon being withdrawn from the donor. The prior art systems have been directed to adding as much anticoagulant as necessary to prevent clotting, with attention being paid to an upper limit dosage of anticoagulant, beyond which a so-called "citrate reaction" may occur in the donor upon return of an anticoagulated blood component to the donor. For example, with same blood separation systems, anticoagulant ratios of up to one part of anticoagulant to eight parts anticoagulated whole blood are used. In plasma collection procedures using the Autopheresis-C ® device, typically six percent anticoagulant is used, but users have the ability to alter this percentage from four percent to eight percent. For platelet collection procedures with the Autopheresis-C ® device, anticoagulant levels of six percent to eight percent are utilized. By the nature of some of these apheresis systems, it would be difficult to separate the four anticoagulant demand stages outlined above and have different amounts added depending on the individual stage.

For example, in the Haemonetics Model 50 Device, there are no intermediate stages in the separation process. If the goal is to make platelet concentrate, the platelet concentrate is derived directly from the whole blood, not from an intermediate component such as platelet-rich plasma for example. In other systems, such as the CS-3000 ® device there are intermediate stages. For example, if plateletpheresis is the objective, platelet-rich plasma is initially separated from whole blood. Then platelet-rich plasma is separated into platelet concentrate. In the CS-3000 ® device, this is done utilizing separate blood component containers within a closed system, within a centrifuge bowl. The Autopheresis-C ® device, in conjunction with a disposable set, separates these components in completely separate stages, but in a single closed system. The platelet-rich plasma is harvested from the donor's blood and the donor is subsequently disconnected. In the next stage, the collected platelet-rich plasma is converted to platelet concentrate and platelet-poor plasma and these become two products of the procedure.

There has been, up until now, no automated blood component separation equipment and procedure for optimizing anticoagulant use during different steps of the automated apheresis procedure. Until now, there has been no recognition of the desirability of reducing the amount of anticoagulant added to whole blood before the separation step. There has been no automated procedure for optimizing the functional characteristics of different blood components in an automated procedure by adding aliquots of anticoagulant or other fluid at different stages in the apheresis procedure.

SUMMARY OF THE INVENTION

According to the present invention, means are provided for adding anticoagulant to a red cell suspension created in an automated blood component sepation procedure, in order to enhance the functional characteristics of one or more blood components.

According to the present invention, anticoagulant is added to incoming whole blood at a location in a defined separation set flow path upstream of the separation chamber, in an amount sufficient to prevent clotting of the whole blood in the flow path upstream of the separator, but in an amount that is insufficient to prevent clotting of the red cell suspension created by the separator. The invention further includes subsequently providing an amount of anticoagulant to the red cell suspension downstream of the separator to prevent clotting.

The purpose of reducing the amount of anticoagulant added to the blood before the blood has been separated is to enhance the functional characteristics of the blood components created by the separator, especially but not limited to an increase in platelet yield during the blood component separation step.

The invention is further directed to a method for increasing platelet yield in an automated blood component separation procedure, in which no anticoagulant is added to whole blood upstream of or at the separator and in which anticoagulant is added to a separator-created component downstream of the separation chamber.

In accordance with the present invention, the amount of anticoagulant added to the whole blood in the automated separation procedure is reduced or eliminated pursuant to our discovery that a decreased amount of anticoagulant results in an increase in platelet yield during the centrifugal separation of blood for example, into a red cell suspension and platelet-rich-plasma. While it is desirable to add anticoagulant or another solution to the collected platelet rich-plasma in order to enhance storage and further separation characteristics of the PRP, the present invention is directed to adding the anticoagulant to the PRP after separation, while reducing or eliminating the amount of anticoagulant in the whole blood prior to separation, in order to enhance platelet yield, along with adding additional anticoagulant to the red cell suspension output from the separation chamber.

In accordance with the present invention a system is provided including means for delivering anticoagulant directly to the separator-created red cell suspension.

While the invention is primarily directed to enhancing platelet yield from a blood separation procedure, it is not limited to this benefit. The invention is directed to adding anticoagulant downstream of a separator in order to prevent the addition of any anticoagulant to whole blood; to the addition of anticoagulant to whole blood in a separation procedure in reduced quantities along with the corresponding addition of anticoagulant to the downstream red cell suspension; and to the addition of anticoagulant to red cell suspension in an automated blood component separation procedure.

DETAILED DESCRIPTION OF THE PREFERRED EMBODIMENTS

Figure 1:
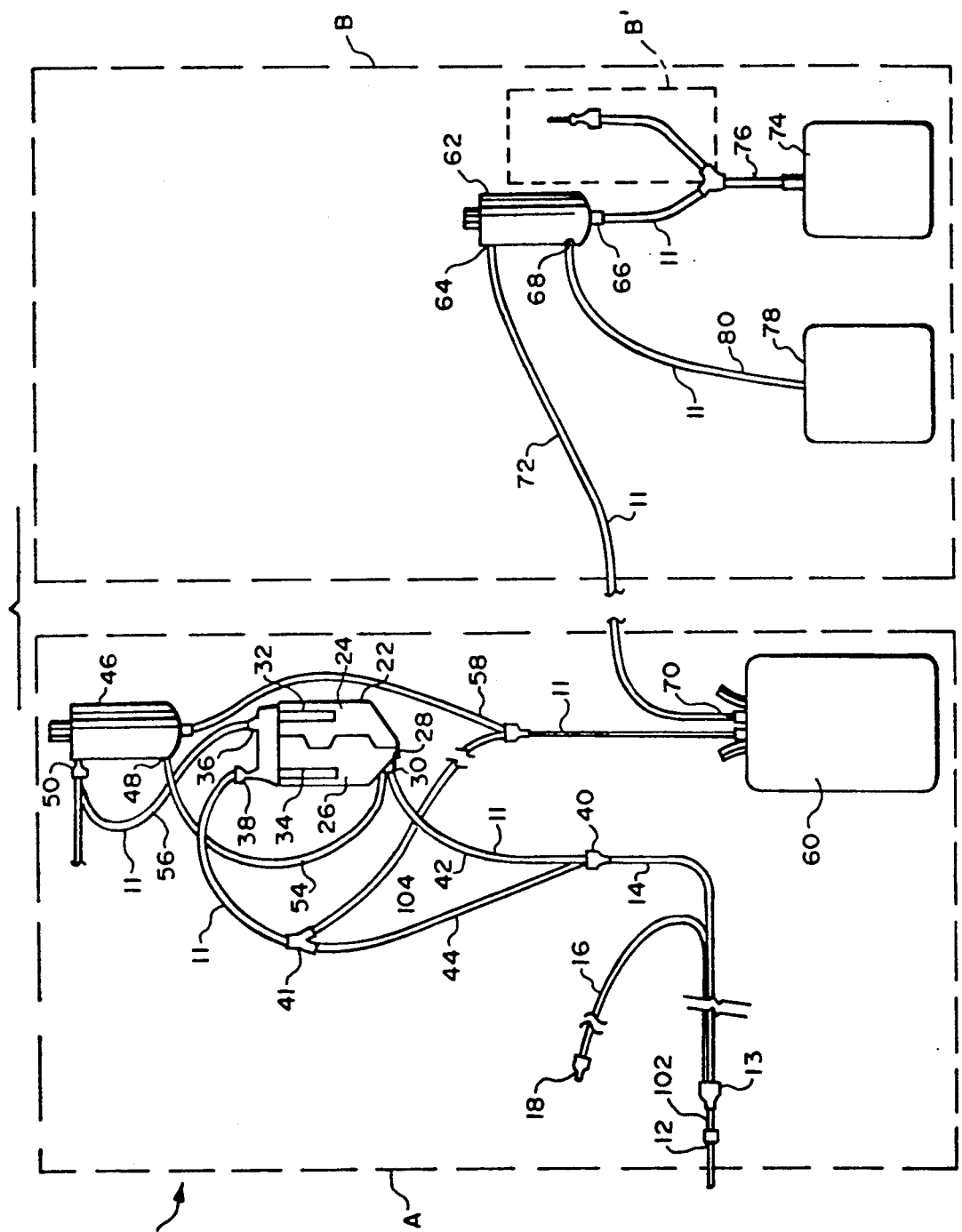
FIG. 1 is a plan view of a tubing/separator set for use in producing platelet concentrate.

Referring now to the drawings, particularly to FIG. 1, there is illustrated a separation set, generally designated 10, such as described in aforementioned U.S. Pat. No. 4,851,126. The set 10 includes tubing 11 and separators 46, 62 defining flow path means. The set 10 may be applied to a microprocessor controlled hemapheresis instrument, such as the instrument H illustrated in FIGS. 2 and 3, in a manner to effect collection of whole blood from a donor through a single needle; separation of the whole blood into packed blood cells and platelet-rich plasma (PRP); reinfusion of the packed blood cells to the donor, (or alternatively, transfer of some of the packed red cells to a red blood cell collection container); and subsequent separation of platelets from the platelet-rich plasma to provide platelet concentrate and cell depleted, platelet-poor plasma (PPP). While in the preferred embodiments the set 10 is described in conjunction with a single needle with its attendant features and advantages, it will be appreciated that the invention is also applicable to two-needle systems.

Set 10 is provided with a single phlebotomy needle 12 for alternately receiving whole blood from a donor and reinfusing one or more blood fractions such as packed red cells back into the donor. The needle 12 communicates with a blood line 14. An anticoagulant line 16 has an anticoagulant spike 18 at one end for reception in an anticoagulant supply container 20, illustrated in FIG. 2. At the opposite end, anticoagulant line 16 joins blood line 14 in a Y-connection 13 closely adjacent the single phlebotomy needle 12.

The set 10 also includes a reservoir 22. The reservoir 22 is divided into a pair of side-by-side compartments 24, 26. Ports 28 and 30 are provided at the lower ends of the compartments 24, 26, respectively. Mesh screen/filter tubes 32, 34 are disposed in compartments 24, 26, respectively, in communication with respective inlet ports 36 and 38 at the upper end of the reservoir 22. The blood line 14 branches, at a Y-connection 40, into branch a line 42 connecting the blood line 14 with the port 28 of compartment 24, and a branch line 44 which connects the blood line 14 with the port 38 of compartment 26. The set 10 additionally includes a separator 46 for separating platelet-rich plasma and packed red cells from anticoagulated whole blood. A separator of this type is described and illustrated in above-identified PCT International Publication WO 88/05332, as wells as in U.S. Pat. No. 4,776,964, Schoendorfer et al., entitled "Closed Hemapheresis System and Methods". For present purposes, separator 46 has a whole blood inlet port 48, a packed cell outlet port 50 and a PRP outlet port 52. The line 54 connects the lower whole blood outlet port 30 of the reservoir compartment 26 with the inlet port 48 of separator 46. A line 56 connects the packed cell outlet 50 of the separator 46 with the inlet port 36 for supplying packed cells to the compartment 24 of the reservoir 22. Tubing 58 connects between the platelet-rich plasma outlet port 52 of the separator 46 and a platelet-rich plasma (PRP) collection container 60.

The foregoing described portion of the set 10 is, for convenience hereafter, identified as the first stage set portion, identified as "A" in FIG. 1, whereas the remaining portion of the set 10 is identified as the second stage set portion, identified as "B" in FIG. 1. The unit labelled "B'" (B prime) in FIG. 1 illustrates an alternate embodiment having a second, return needle to the donor. It will be appreciated from this description that the first and second stage portions A, B form an integral or unitary set 10 which is packaged and sold for one-time use with the instrument H disclosed in FIGS. 2 and 3 hereof.

The second stage portion of set 10 also includes in use the PRP container 60 which serves as the platelet-rich plasma supply from which platelets are concentrated upon installation of the second stage portion B on instrument H, as described hereinafter. The second stage portion also includes a separator 62 of the rotary filter membrane type, such as described and illustrated in previously identified Canadian Patent No. 1,261,765. For present purposes, the separator chamber 62 filters the platelet-rich plasma received from the container 60 to provide platelet concentrate and depleted or platelet-poor plasma filtrate (PPP). The separator 62 has a platelet-rich plasma inlet port 64, a platelet-poor or cell depleted plasma outlet port 66 and a platelet concentrate outlet port 68. The container 60 has a PRP outlet port 70 in communication with the inlet port 64 of the separator 62 via tubing 72. A platelet-poor plasma collection container 74 communicates with the outlet port 66 of the separator 62 via tubing 76. Finally, the platelet concentrate outlet port 68 of the separator 62 communicates with a platelet concentrate collection container 78 via tubing 80.

As an alternative, the platelet-rich plasma tubing 72 may be connected to the lower tangential port 68 of the separator 62 and the platelet concentrate tubing 80 may be connected to the upper tangential port 64 of the separator 62. The separator will operate to provide platelet concentrate using this alternate connection. However, the illustrated embodiment is preferred because it facilitates ready removal of the final aliquot of blood product from the separator 62 at the end of the procedure.

As indicated previously, the set 10 is disposable and preferably each of the first and second stage portions are separately provided in discrete flexible plastic containers or pouches indicated by the dashed lines designated A and B, respectively, in FIG. 1. Thus, when the first stage portion is used in conjunction with the instrument illustrated in FIGS. 2 and 3, as hereinafter described, the second tubing portion may be retained in its plastic container or pouch B and disposed on an available hook on the instrument until the first stage portion is removed from the instrument and the second stage portion is applied thereto. It will be understood, however, that the first and second stage portions of the set 10 are integrally connected one to the other and comprise a single closed blood collection, reinfusion and separation system. Accordingly, while the first and second stage portions A, B may be provided in discrete pouches, they are interconnected and their provision in discrete pouches is for convenience of use only as will be apparent from this description.

Figure 2:
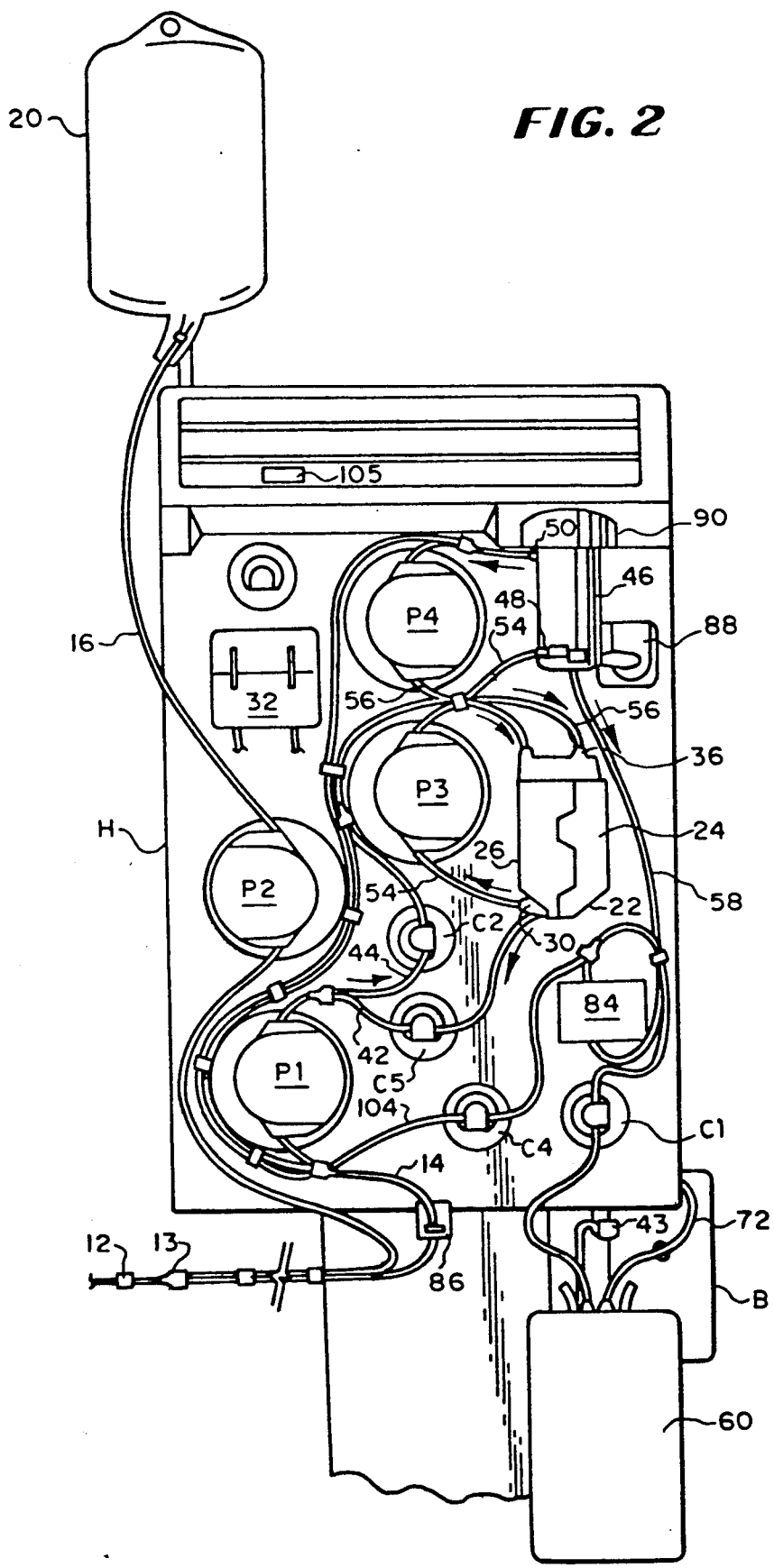
FIG. 2 is a front elevational view of a microprocessor-controlled, automated blood component separation instrument illustrating a first stage of the set of FIG. 1 installed in the instrument.
Figure 3:
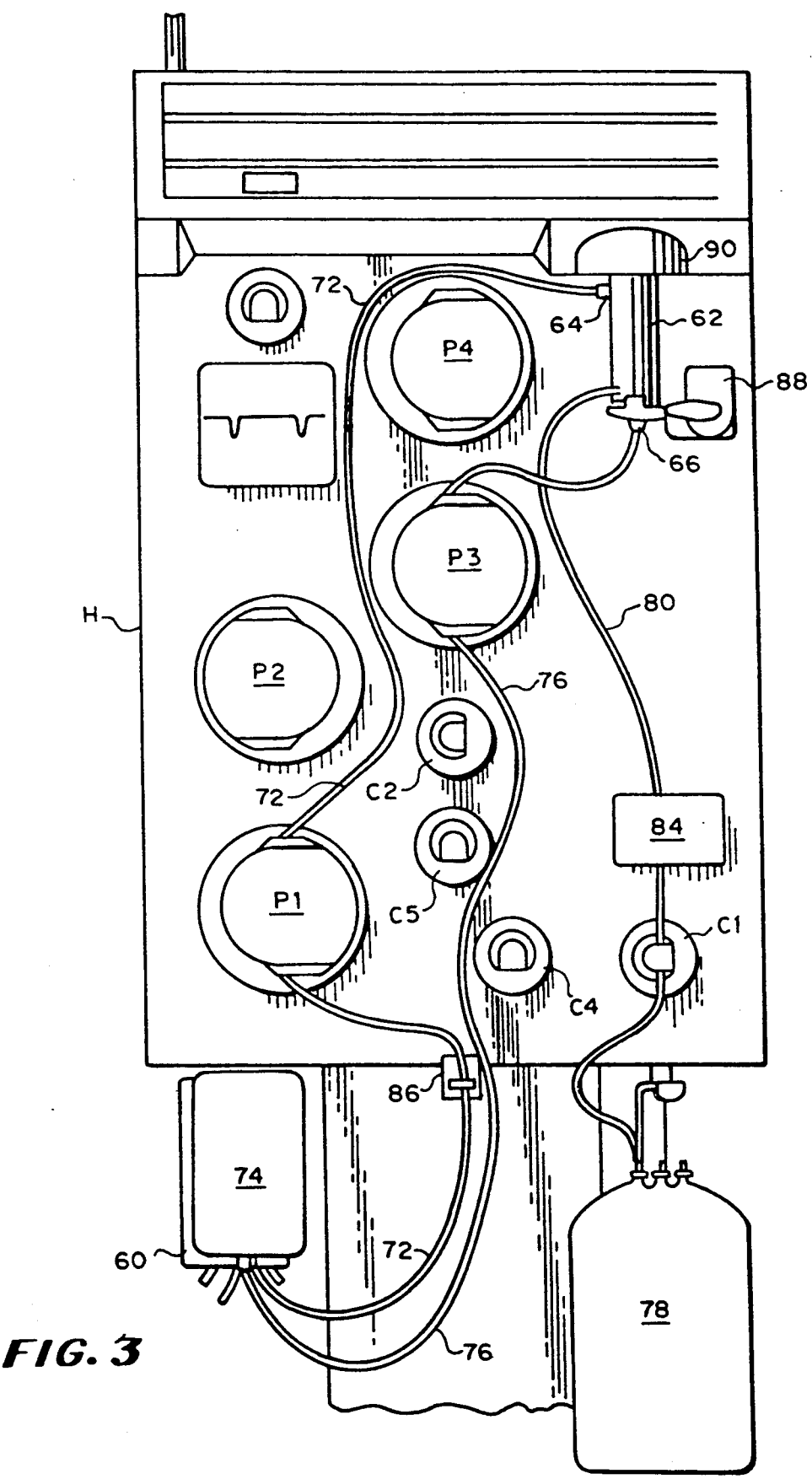
FIG. 3 is a front elevational view illustrating the instrument with a second stage of the set of FIG. 1 installed in the instrument.
Figure 4:
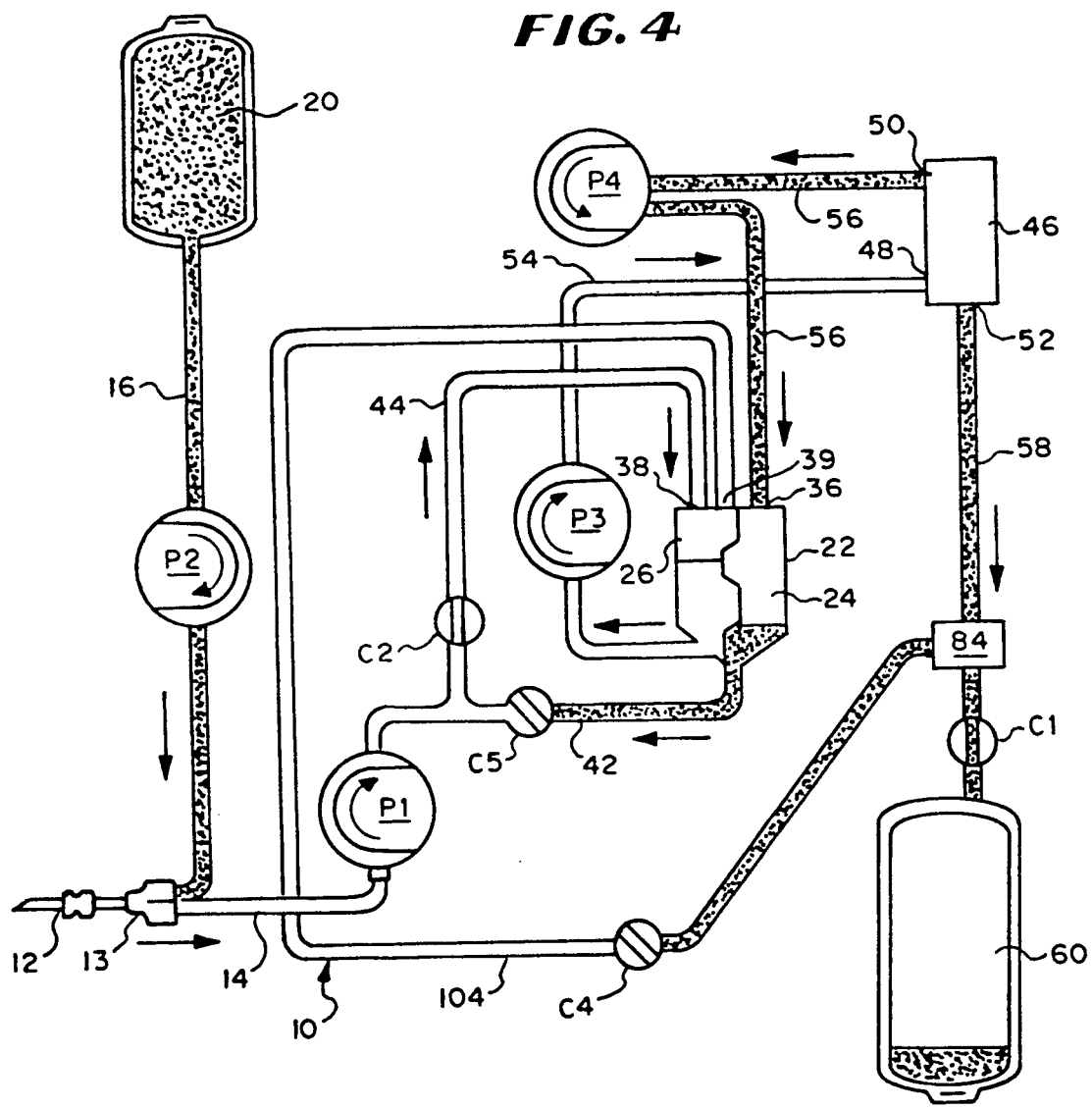
FIG. 4 is a schematic/fluid flow diagram of the blood withdrawal and separation cycle of the first stage portion of the set installed in the instrument as shown in FIG. 2.
Figure 5:
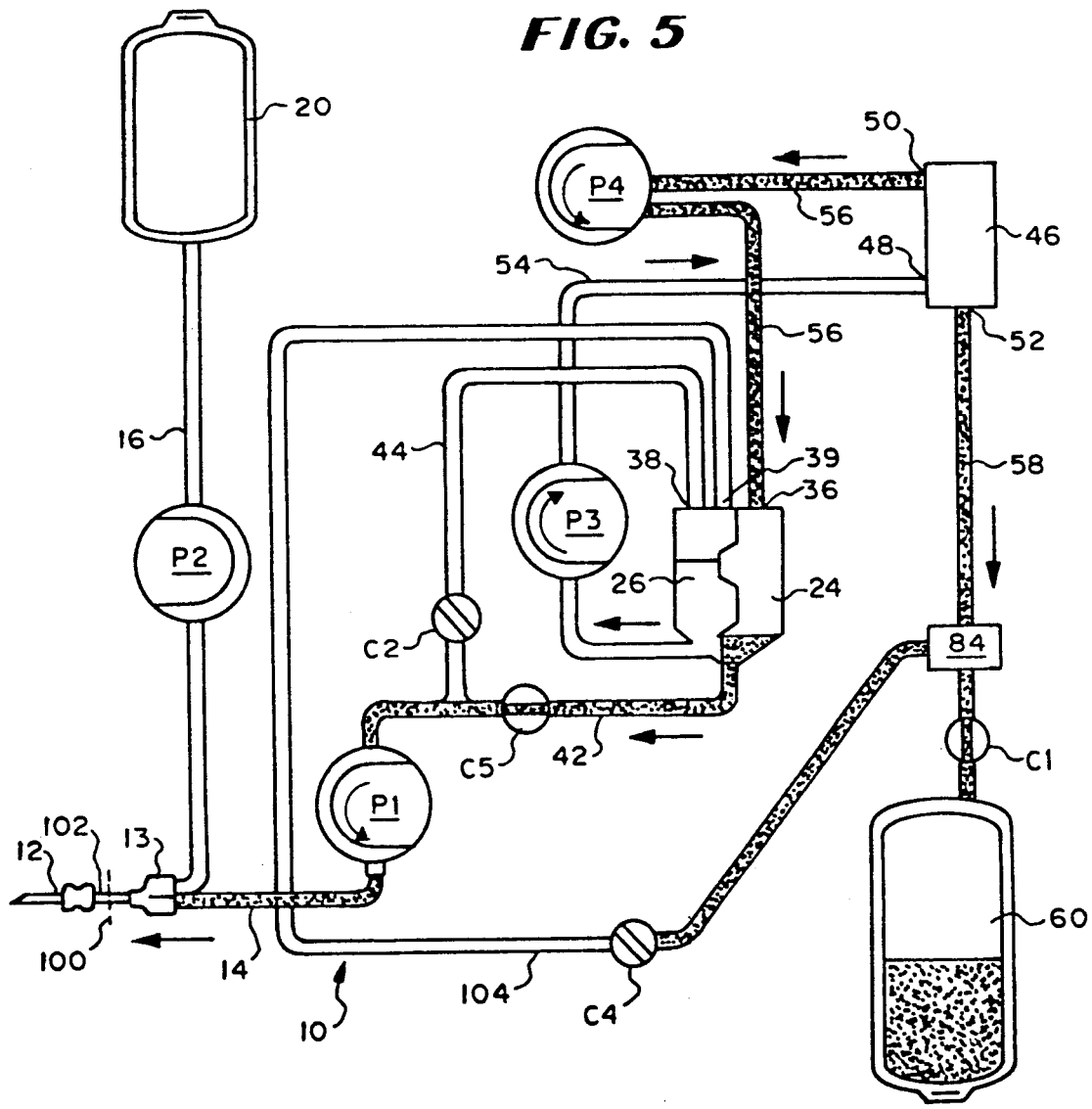
FIG. 5 is a schematic/fluid flow diagram of the separation and reinfusion cycle of the first stage portion of the set as shown in FIG. 2.

Turning now to FIGS. 2 and 3, and especially FIGS. 4 and 5, the relevant operating components of the hemapheresis instrument H will now be described. The instrument is provided with various pumps, detectors, clamps, and the like, under control of a microprocessor, for cooperation with the set 10 when applied to the instrument. As illustrated in FIGS. 2, 4 and 5, there are provided pumps P1, P2, P3 and P4 on the front face of instrument H. These pumps are preferably of the peristaltic type and cooperate with the various tubings 11 of the set to flow blood in the desired directions between the various elements of the set. Also, a series of clamps are provided which receive various tubing segments of the set 10. The clamps are movable between open or closed positions and thus operate to open or close the lumens of the tubing segments disposed in the clamps. For present purposes, only clamps C1, C2, C4 and C5 need be identified. The face of the instrument also contains a pressure transducer 82, a hemoglobin detector 84, an air detector 86, sensors (not shown) for determining the levels of liquid in reservoir 22, and a mount or lower holder 88 for the separators 46 and 62 of the harness set 10. The face of instrument H also includes a motor cup 90 for mounting motor magnets which, in turn, drive the separator rotors. Thus, separators 46 and 62 may be installed sequentially on lower mount 88 with their upper ends in the motor cup, whereby magnetic connection is effected between the magnetic drive motor and the rotor of the installed separator.

In accordance with the method of separating blood into constituent parts the first stage portion of set 10 is applied to the instrument face, while the second stage portion is preferably retained in its pouch B and hung from an available hook on the instrument. Under control of the microprocessor, instrument H operates the pumps, clamps, detectors and the like in conjunction with the first stage portion of set 10 to separate platelet-rich plasma from whole blood and reinfuse packed red cells into the donor. During this separation procedure, anticoagulant is metered into whole blood being withdrawn from the donor. After the PRP has been collected, the phlebotomy needle is removed from the donor and additional anticoagulant is delivered to the PRP. The first stage portion is then removed from the instrument, separated from the second stage portion and discarded. The second stage portion of the set is then installed in the instrument H as shown in FIG. 3 to generate platelet concentrate from the platelet-rich plasma. The procedure of ultimately providing platelet concentrate will now be described in detail, including the known procedure steps such as disclosed in U.S. Pat. No. 4,851,126 as well as the new method steps and apparatus for addition of anticoagulant.

Referring to FIGS. 2 and 4, the various tubings 11 of the first stage portion A are applied to instrument H as follows: blood line 14 is disposed in blood pump P1; lines 42 and 44 are disposed in clamps C5 and C2, respectively; line 54 is applied to pump P3 and line 56 is applied to pump P4. The reservoir 22 is mounted on the face of the instrument, by means not shown, and the separator 46 is disposed on the mount 88 with its upper end disposed in the motor cup 90 such that the drive rotor of separator 46 is coupled magnetically to the drive motor of the instrument. Platelet-rich plasma line 58 is disposed in hemoglobin detector 84 and clamp C1 and platelet-rich plasma container 60 is hung from a weight scale on a lower part of the instrument.

Divert line 104, which extends from the PRP line 58 to the compartment 26 at port 39 (FIG. 4), is mounted in clamp C4. Alternatively, but not important for the purpose of the present invention, as seen in FIGS. 1 and 2 the divert line 104 may instead join the branch line 44 at Y-connector 41, for return to the compartment 26 at port 38.

Anticoagulant line 16 is disposed in anticoagulant pump P2 and is connected at one end to a supply of anticoagulant, i.e., supply container 20, for supplying anticoagulant via line 16 to blood line 14 adjacent the needle 12. The blood line 14 also extends through the air detector 86. The second stage portion is retained in its individual pouch B which is hung from an available hook on the instrument in an out-of-the-way location.

In operation, various procedures are followed under control of the microprocessor for performing certain instrument functions which need not be described herein. Referring to FIG. 4, after set-up and following venepuncture performed on the donor and after priming of the separator and reservoir, the instrument, in conjunction with the first stage portion A, is ready to alternately collect whole blood from the donor and reinfuse packed red cells into the donor while whole blood is simultaneously and continuously supplied to the separation device to produce platelet-rich plasma and packed cells. Thus, clamp C2 is opened, clamp C5 is closed and pumps P1, P2, P3 and P4 are actuated. Whole blood therefore flows through the needle 12 and blood line 14, through open clamp C2, and into whole blood compartment 26 via branch line 44 and inlet port 38 of reservoir 22.

Anticoagulant, such as known anticoagulant citrate dextrose solution Formula A (ACDA), is added to the whole blood by pump P2 via line 16 at its Y-connection with blood line 14. This known anticoagulant includes dextrose (hydrous), sodium citrate (hydrous) and citric acid (anhydrous). Other anticoagulants can also be used in accordance with medical guidelines for various anticoagulant formulations.

Closed clamp C5 prevents flow of anticoagulated blood into reinfusion line 42. Pump P3 pumps whole blood from compartment 26 through outlet port 30 via line 54 into separator 46 via inlet port 48. Red cells are pumped from separator 46 through outlet 50 via line 56 by pump P4 into reservoir compartment 24 through inlet port 36. Platelet-rich plasma flows from separator 46 via line 58 through hemoglobin detector 84 and open clamp C1 into collection container 60. Divert clamp C4 is closed. Thus, during collection anticoagulated whole blood is supplied to compartment 26 and separator 46 while packed cells are supplied to compartment 24 and platelet-rich plasma is supplied to container 60.

The system provides for the alternate collection of whole blood from the donor and reinfusion of packed cells or platelet-depleted plasma into the donor while separator 46 simultaneously and continuously receives anticoagulated whole blood for separation into the platelet-rich plasma and packed cells. To accomplish this, sensors, not shown, on the instrument face detect the level of fluids in the compartments 24, 26 of the reservoir 22. When the compartments are full, the microprocessor, in response to the detected signals, causes instrument H to change from its blood collection cycle to its reinfusion cycle.

Referring now to FIG. 5, in the reinfusion cycle, clamp C2 is closed and clamp C5 is opened and the anticoagulant pump P2 is stopped. Pump P1 is reversed to pump packed cells from compartment 24 of reservoir 22 into the donor through needle 12. Pumps P3 and P4, however, continue to operate to respectively provide anticoagulated whole blood from the compartment 26 of reservoir 22 to separator 46 and to supply packed cells from separator 46 to compartment 24 of reservoir 22. When the packed cells and the supply of whole blood are substantially depleted from compartments 24 and 26, respectively, these low liquid levels are sensed. At that time, the microprocessor causes instrument H to change from its reinfusion cycle back to its blood collection cycle. Thus, clamp C2 is opened, clamp C5 is closed, pump P2 is started, and pump P1 is reversed to again begin the draw cycle illustrated in FIG. 4, with anticoagulated whole blood flowing to the whole blood compartment 26, which has been substantially depleted of whole blood during the reinfusion cycle illustrated in FIG. 5. It will be appreciated that during the alternate collection and reinfusion cycles, whole blood is continuously pumped from reservoir compartment 26 to separator 46 by pump P3 whereby separation is effected continuously. Thus, platelet-rich plasma (PRP) flows continuously from separator 46, while anticoagulated whole blood is continuously supplying separator 46.

In the preferred embodiments, PRP collection terminates when a preselected weight of PRP has been reached utilizing a weight scale 43. The preselected weight value may be selected by the operator for donor-specific reasons such as donor weight, donor age, etc.

When the preselected PRP weight value in the container 60 is reached, the instrument automatically transfers to a final return mode including purging the tubing 11 of all but a small, amount of packed cells (e.g. about 10 mls). Then, the instrument automatically notifies the instrument operator to disconnect the donor. The operator uses a hemostat 100 or other known clamp to close the tubing segment 102 that is disposed between the phlebotomy needle 12 and the connector 13 which joins anticoagulant supply line 16 and the blood line 14. The operator may then remove the phlebotomy needle from the donor's vein. The donor may rest and then leave. The hemostat 100 is illustrated schematically in FIGS. 5 and 6.

Figure 6:
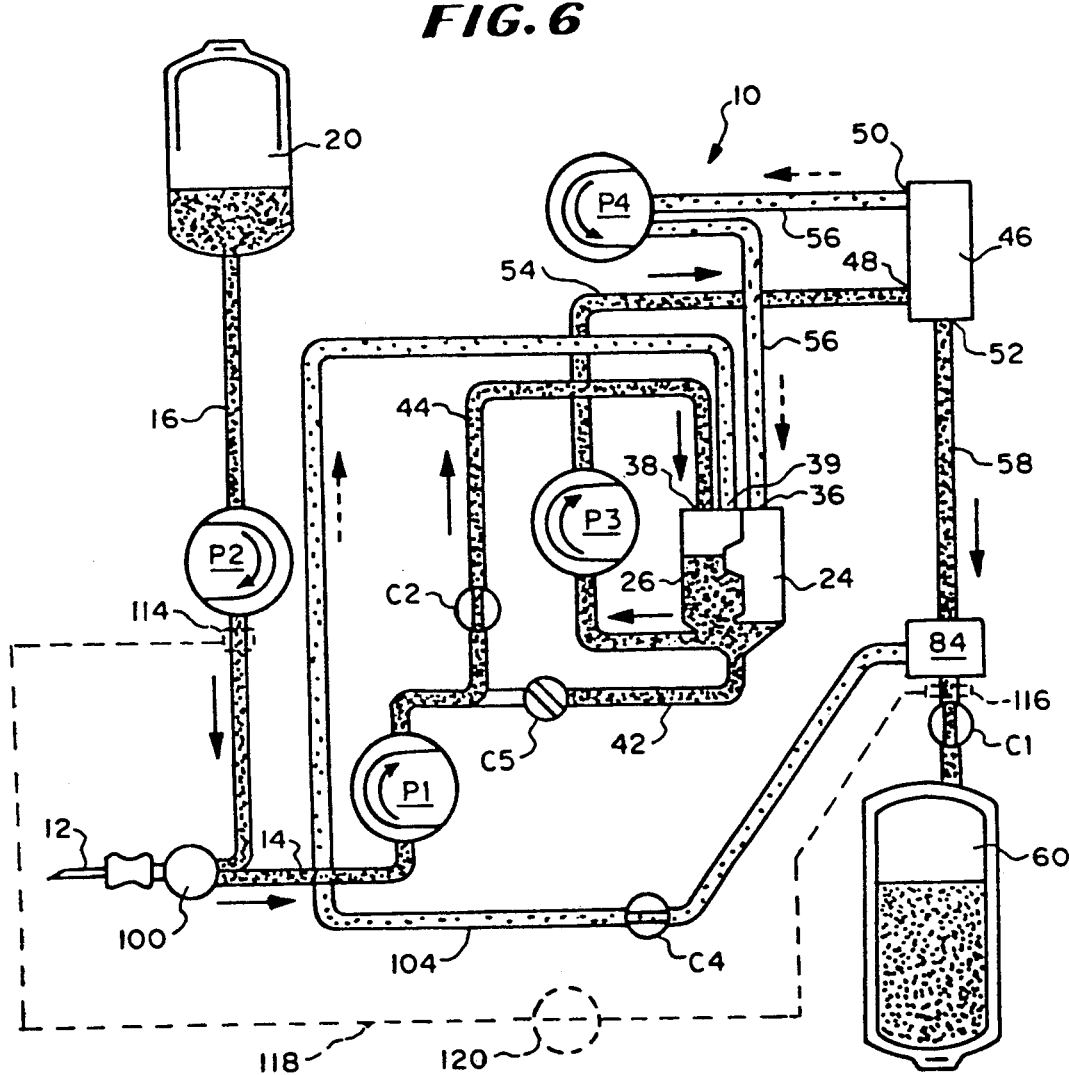
FIG. 6 is a schematic/fluid flow diagram of the first stage portion of the set, illustrating introduction of a second aliquot of anticoagulant into the PRP.

Next, the operator activates an advance button 105 on the instrument H that notifies the microprocessor control in the instrument that the donor has been disconnected. The microprocessor control then automatically advances the procedure into the new PRP-anticoagulant addition cycle illustrated in FIG. 6, so as to deliver an additional amount of anticoagulant to the PRP in the container 60. This cycle is controlled by the microprocessor in the instrument. As seen in FIG. 6, pumps P1, P2 and P3 are activated. Pumps P1 and P2 pump at a speed of about 15 mls per minute, at most about 250 mls totally, of anticoagulant through line 16 into blood line 14 and, as in the draw cycle illustrated in FIG. 4, clamp C2 is open and clamp C5 is closed so that pump P1 pumps anticoagulant from source 20 through branch line 44 into compartment 26 through the port 38. Input pump P3 pumps the anticoagulant from the compartment 26 into the separator 46 through tubing line 54 along with significant residual red cells in the tubing and reservoir. Pump P3 may operate at a speed of about 15 mls per minute, for example. Preferably output pump P4 is not operated. Therefore, additional packed cells accumulate within the separator 46. The rotor within the centrifugal separator 46, which normally operates in the range of approximately 2400 to 3600 rpm during the separation procedure, here operates at a speed of approximately 2000 rpm.

As the anticoagulant mixed with the residual blood cells enter by line 54 into the separator 46, where additional red cells reside, the centrifugal force within the separator separates the anticoagulant from these cells in the same manner that the separator operates to separate PRP from the donor's whole blood during the above-described separation procedure. The separated anticoagulant exits the separator 46 through port 52 and line 58, which is disposed within the hemoglobin detector 84.

The system has been stopped for a time period in order to enable the operator to disconnect the donor from the instrument and set. Thus, the efficiency of the separator 46 will initially be less than optimal when the PRP-anticoagulant addition cycle illustrated in FIG. 6 begins. Therefore, it is likely that the first aliquot of anticoagulant flowing through line 58 during the PRP-anticoagulant addition step will have an unacceptably high concentration of red cells. If so, the hemoglobin detector 84, through the microprocessor control, will close the platelet line clamp C1 and open the divert clamp C4, thereby diverting the packed cell/anticoagulant mix through divert tubing line 104 back into the reservoir compartment 26 via port 39, for subsequent recirculation into the separator 46 through the tubing line 54. As previously mentioned and as shown in FIG. 2, the divert line may alternatively join branch line 44 to reach compartment 26 via port 38.

After a short time period (approximately 30 seconds) the separator 46 will be operating with sufficient efficiency so as to meet the low hemoglobin standard set by the detector 84. Upon sensing the lower hemoglobin content, the detector 84 will instruct the microprocessor to close clamp C4 and open clamp C1, thereby delivering the desired additional aliquot of anticoagulant to the platelet-rich plasma previously collected in the collection container 60.

By not operating the pump P4, the packed cells tend to remain in the separator, thereby lessening the volume of anticoagulant and therefore the time required to perform the PRP-anticoagulant addition step shown in FIG. 6. The centrifugal separator itself has a low blood volume of about 15 mls. If the final tubing purge performed immediately prior to donor disconnect leaves more than the desired volume of red cells in the set 10, this may result in higher pressure within the separator 46 than is desirable for the selected efficiency range of the separator during the PRP-anticoagulant addition step. If the pressure is higher than about 320 mmHg, the pump P4 may be activated at a slow pumping rate, such as at a rate of 15 mls per minute, thereby returning some of the packed cells from the separator 46 into the reservoir compartment 24, through port 36, until the device pressure is released.

By means of the just described PRP-anticoagulant addition procedure, the PRP receives the necessary nutrients and pH buffering for PRP storage, at least equivalent to that performed by prior art procedures where all anticoagulant is added to the whole blood during the draw cycle from the donor. In addition, this system permits the reduction of the amount of anticoagulant added to the whole blood, with two very significant results: (1) increased platelet yield and (2) reduced chance of a citrate response in the donor.

First, it has been discovered that the decreased anticoagulant concentration in the whole blood being separated in the separator during both the draw and reinfusion cycles illustrated in FIGS. 4 and 5 results in greater platelet yield, a highly desirable goal. Typically, with the Autopheresis-C ® instrument operators have utilized eight or six percent anticoagulant level in the whole blood. With the new, PRP-anticoagulant addition procedure, the anticoagulant added to the whole blood during the draw/separation cycle may be reduced, for example to a level of approximately 4 percent anticoagulant.

In this specification the anticoagulant levels indicate the percent anticoagulant by volume for anticoagulant-added whole blood. Stated differently, an 8% level means 8 parts anticoagulant to 92 parts whole blood, or 8 parts anticoagulant in 100 parts anticoagulated whole blood. This is the standard system for comparing anticoagulant levels in the medical community. Furthermore, while anticoagulant levels in separated blood fractions vary, comparisons have typically been made by looking at the anticoagulant level in the whole blood to be separated.

The level of anticoagulant added to blood components by the instrument A can be precisely controlled by the use in the instrument of the pump calibration system disclosed in U.S. Pat. No. 4,769,001, assigned to the assignee of the present invention.

Tables I and II illustrate the improvement in platelet yield in the separated PRP achieved by lowering the anticoagulant level supplied to the whole blood during the draw/separation cycle of FIG. 4, made possible by the later, PRP-anticoagulant addition cycle.

TABLE II

| Donor | % Change in Yield Over 8% | |
|---|---|---|
| | At 6% | At 4% |
| 1 | 15 | 39 |
| 2 | 21 | 42 |
| 3 | 21 | 31 |
| 4 | 57 | 61 |
| 5 | 6 | −7 |
| 6 | 18 | 1 |
| 7 | 7 | 36 |
| 8 | 36 | — |
| 9 | 30 | 68 |
| 10 | 11 | 21 |
| 11 | 11 | — |
| 12 | 24 | 27 |
| 13 | 16 | 19 |
| 14 | 15 | 29 |
| Average | 21 | 31 |

| Donor | % Change in Yield Over 6% |
|---|---|
| | At 4% |
| 15 | 3 |
| 16 | 8 |
| 17 | 0 |
| 18 | 46 |
| Average | 14 |

Referring to Table I, PRP efficiency is a relevant parameter to show improvement in platelet yield. To calculate PRP efficiency, the volume of platelet rich plasma collected is multiplied by the platelet concentration in that platelet rich plasma, the product forming the numerator. The denominator used in determining PRP efficiency is the product of the platelet concentration in the donor's anticoagulated whole blood (the precount) times the volume of blood that was processed in the procedure.

In the fourteen donors 1 through 14, mean PRP efficiency improved from 42 to 47 to 48 percent at antico-

TABLE I

| | 8% ACDA Anticoagulant | | | 6% ACDA Anticoagulant | | | 4% ACDA Anticoagulant | | |
|---|---|---|---|---|---|---|---|---|---|
| Donor | PRP Efficiency Total Collected (%) | Precount Platelet Concentration In Donor's Anticoagulated Whole Blood (/ul) | Platelet Concentration In Collected PRP (/ul) | PRP Efficiency Total Collected (%) | Precount Platelet Concentration In Donor's Anticoagulated Whole Blood (/ul) | Platelet Concentration In Collected PRP (/ul) | PRP Efficiency Total Collected (%) | Precount Platelet Concentration In Donor's Anticoagulated Whole Blood (/ul) | Platelet Concentration In Collected PRP (/ul) |
| 1 | 45 | 198200 | 507600 | 46 | 220040 | 584400 | 49 | 244000 | 704672 |
| 2 | 50 | 251400 | 686000 | 50 | 271750 | 828750 | 52 | 285500 | 972931 |
| 3 | 41 | 207667 | 540667 | 55 | 211250 | 655250 | 51 | 237333 | 709256 |
| 4 | 40 | 299333 | 697667 | 33 | 428000 | 1095000 | 43 | 441500 | 1121648 |
| 5 | 46 | 273000 | 703286 | 49 | 280000 | 744000 | 43 | 284000 | 652000 |
| 6 | 43 | 182200 | 465000 | 69 | 163000 | 550000 | 57 | 222000 | 468000 |
| 7 | 37 | 306800 | 628200 | 33 | 330000 | 671000 | 40 | 367000 | 853889 |
| 8 | 36 | 228250 | 660250 | 39 | 314000 | 899000 | | | |
| 9 | 39 | 238000 | 510000 | 46 | 252000 | 665000 | 58 | 282000 | 855000 |
| 10 | 37 | 202500 | 596500 | 45 | 214000 | 665000 | 44 | 217500 | 723188 |
| 11 | 48 | 233000 | 645000 | 48 | 233667 | 714667 | | | |
| 12 | 45 | 178000 | 406000 | 49 | 189500 | 502000 | 44 | 206500 | 516712 |
| 13 | 45 | 298750 | 798500 | 45 | 328000 | 929500 | 45 | 318000 | 951500 |
| 14 | 41 | 324800 | 798600 | 51 | 316750 | 919750 | 49 | 362000 | 1034000 |
| N | 14 | 14 | 14 | 14 | 14 | 14 | 12 | 12 | 12 |
| x | 42 | 244421 | 617376 | 47 | 267997 | 744523 | 48 | 288944 | 796900 |
| SD | 4 | 48947 | 119197 | 9 | 70576 | 168231 | 6 | 71794 | 202818 |
| 15 | | | | 48 | 191000 | 594500 | 58 | 161500 | 617922 |
| 16 | | | | 53 | 363333 | 787000 | 56 | 226500 | 621272 |
| 17 | | | | 49 | 197000 | 566333 | 45 | 180000 | 566871 |
| 18 | | | | 38 | 238000 | 531000 | 65 | 238000 | 773471 |
| N | | | | 4 | 4 | 4 | 4 | 4 | 4 |
| x | | | | 47 | 247333 | 619708 | 56 | 201500 | 644884 |
| SD | | | | 6 | 80104 | 114514 | 8 | 36604 | 89266 |

N = Total Donors
x = Mean PRP Efficiency
SD = Standard Deviation agulant levels of 8 percent, 6 percent, and 4 percent respectively.

Donors 15 through 18 were run at anticoagulant levels of 6 percent and 4 percent resulting in a mean PRP efficiency of 47 percent and 56 percent respectively.

The data could be presented without platelet concentration in both precount and PRP, illustrating only the effect of the anticoagulant concentration on PRP efficiency. However, this would overlook the benefit of less anticoagulant diluting the blood less, thereby allowing the system to start with a higher precount.

Table II is a summary illustrating the percentage change in platelet yield at different anticoagulant levels. Platelet yield is the platelet count in the PRP. Yield comparisons are made utilizing constant volume of PRP. When collecting platelets, it is desirable to maximize platelet yield.

We have found that by lowering the whole blood anticoagulant level from 8 percent to 6 percent, there is an increase in platelet yield of approximately 21 percent. Approximately half of the 21 percent increase is due to less fluid volume because of less anticoagulant and about half of the 21 percent increase is due to other factors, currently unexplained, which may be occurring within the separator because of the reduced anticoagulant level. Similarly, a reduction from 8 percent to 4 percent anticoagulant in the withdrawn whole blood results in an approximately 31 percent improvement in platelet yield, approximately half of which results from the reduced fluid volume. The other half of the improvement is caused by other reasons.

The second significant beneficial effect of lowering the anticoagulant level in the whole blood is that it greatly reduces the likelihood of an adverse citrate reaction in the donor. Citrate reaction is a known condition that occurs when the amount of anticoagulant returned to the donor becomes too high. This value differs from donor to donor. The problem is exacerbated during a platelet collection procedure, as opposed to plasma collection, for the following reasons.

Anticoagulant is soluble in plasma. In any manual or automated plasma collection procedure, i.e. a procedure wherein it is desirable to have the platelets remain with the packed cells (plasma collection) as opposed to remaining with the plasma (for e.g. platelet collection), the hematocrit (i.e. the packed cell concentration) is typically higher than with a platelet collection procedure such as has been set forth above. Typically, with the Autopheresis-C ® system, an expected hematocrit valve for packed cells returned to the donor in a plasma collection procedure is about 70. However, in a platelet collection procedure as described above, the resulting hematocrit valve for the packed cells is typically less, on the order of about 55 for a typical donor.

Stated differently, the percentage that comprises plasma of the entire packed cell suspension returned to the donor in the platelet collection procedure is more than the percentage of plasma in the packed cell suspension returned to the donor in a plasma collection procedure. Thus, because anti-coagulant is plasma-soluble, for a given amount of anticoagulant added to the whole blood, the amount of anticoagulant in the packed cell suspension returned to the donor in a platelet collection procedure is higher than in a plasma collection procedure.

This alone is a significant reason for why adverse, citrate reactions are more likely to occur in platelet collection procedures than in plasma collection procedures. The problem becomes more egregious in platelet collection operations performed by prior art methods because of the typically higher anticoagulant levels in the whole blood which were sought in order to obtain a higher anticoagulant level in the platelet-rich plasma, the goal being to meet previously described storage condition requirements for the platelet concentrate.

The new, PRP-anticoagulant addition step set forth herein satisfies the storage requirements for collected platelets as achieved by the prior art, while providing the additional benefits of increased platelet yield and reduced incidence of citrate reaction in the donor.

These benefits are achieved with the new method described above, (1) even though most blood separation procedures generate stress on the platelets so that the platelets exiting the separation chamber are partially activated, thereby requiring sufficient anticoagulant to eliminate clotting which otherwise occurs; and (2) even though in platelet collection procedures, such as the procedure described above, significant numbers of platelets, partially activated, are returned with the red cells to the donor.

Thus, the PRP-anticoagulant addition step permits adding about 4 percent or less anticoagulant to the donor's whole blood, which is just enough to sufficiently anticoagulate the system and yet enjoy the high performance and platelet yield resulting from such a low anticoagulant level. The subsequent addition of anticoagulant to the PRP permits adequate storage of the platelet concentrate product after separation from the plasma.

While FIG. 6 and the accompanying description set forth a preferred embodiment for adding anticoagulant to the collected PRP as the PRP-anticoagulant addition method, in particular by routing anticoagulant through the separation chamber 46, it will be appreciated that other means can be provided for accomplishing the addition of anticoagulant to the collected PRP. For example, a less preferred, alternate embodiment is set forth in phantom line in FIG. 6. In the alternate embodiment, a Y-connector 114 is disposed in the anticoagulant line 16 downstream of pump P2. Another Y-connector 116 is disposed in the PRP outlet line 58 downstream of the hemoglobin connector 84. A tubing segment 118 is disposed between the two Y-connectors. An associated hardware clamp 120 selectively closes and opens the tubing segment 118, for the selective addition of anticoagulant to the container 60 through the tubing segment 118. This sort of configuration, while providing a more direct routing of anticoagulant to the container 60, results in a change to the disposable which is otherwise not needed as well as the addition of an extra clamp in the hardware. In addition, such a configuration does not take advantage of separating the small aliquot of remaining blood in the reservoir 22, unlike the preferred procedure as set forth in FIG. 6, wherein the anticoagulant in the PRP-anticoagulant addition procedure runs through the separation chamber 46.

Figure 7:
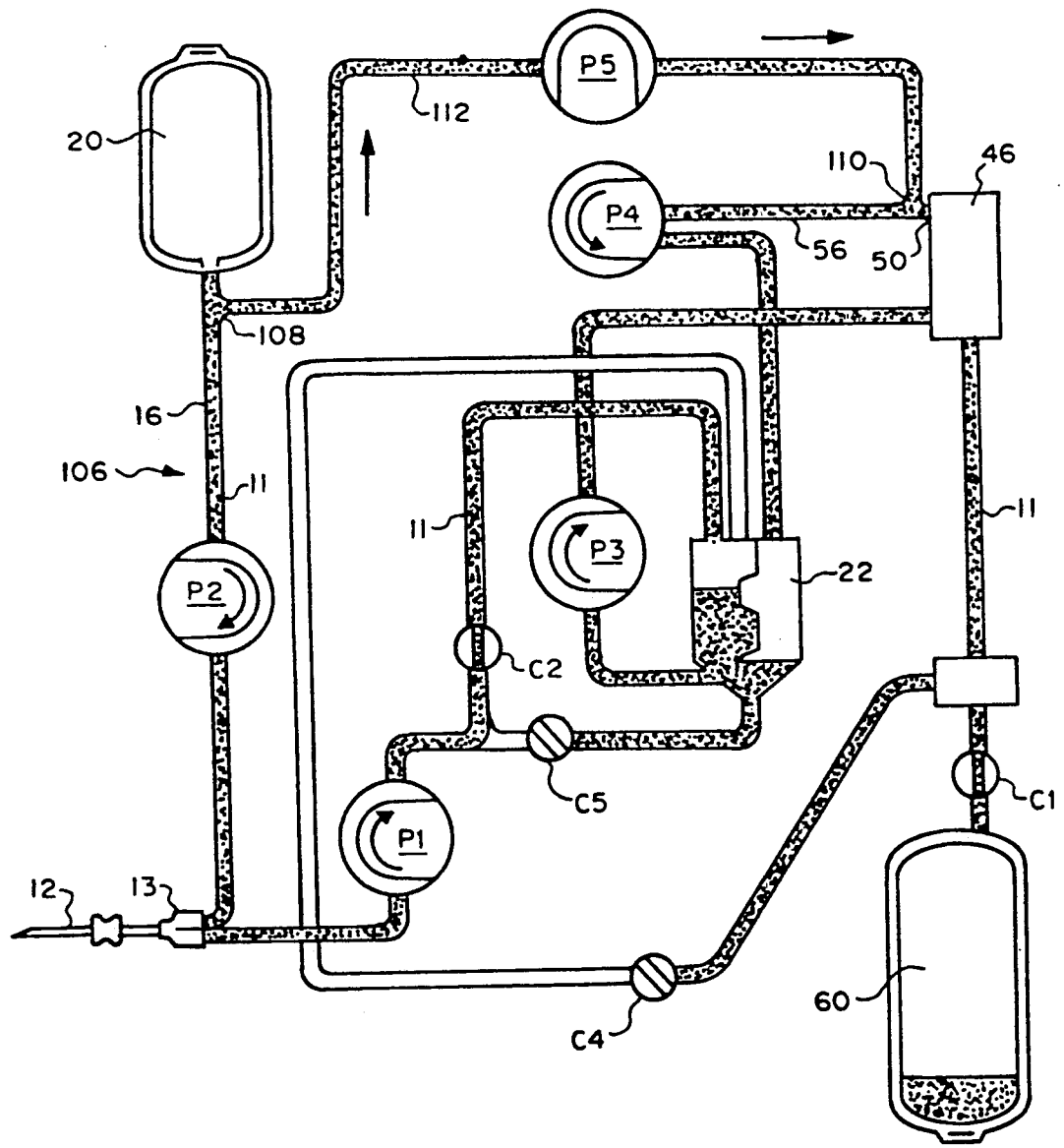
FIG. 7 is a schematic/fluid flow diagram of another first stage set portion for introducing a subsequent aliquot of anticoagulant into the PRP.

Still further improvements are obtained by means of the blood processing system illustrated in FIG. 7. Here, like numbers are used for like components compared to the previous embodiment. In FIG. 7 there is shown a set 106 that is utilized with the microprocessor-controlled instrument H.

The set 106 includes the separator 46, reservoir 22, PRP collection container 60, phlebotomy needle 12 and tubing 11 as set forth in the embodiment of FIGS. 1 through 6. A Y-connection 108 is disposed in the anticoagulant tubing 16 between the anticoagulant supply 20 and the pump P2. A Y-connection 110 is provided in tubing line 56 between the separator outlet port 50 and the output pump P4. Secondary anticoagulant line 112 communicates between anticoagulant line 16 and line 56 via Y connectors 108 and 110. The instrument H includes an additional pump P5, which serves as a secondary anticoagulant pump.

Set 106 is installed in the instrument H as set forth previously. Additionally, tubing line 112 is installed in the secondary anticoagulant pump P5. Operation of the set 106 during a blood separation procedure is best understood by reference to FIGS. 4 and 5 as well as FIG. 7. Primary anticoagulant pump P2 is a discontinuous pump in that it operates only during the draw cycle illustrated in FIG. 4. In contrast, the secondary anticoagulant pump is a so-called continuous pump in that it operates under microprocessor control, during both the draw and separation cycle illustrated in FIG. 4 and the reinfusion and separation cycle illustrated in FIG. 5. During both draw and reinfusion, the secondary anticoagulant pump P5 meters anticoagulant by pumping it from the supply source 20 through tubing 112 into the tubing line 56. Anticoagulant entering the tubing line 56 from the tubing line 112 is pumped by pump P4 into compartment 24 of the reinfusion reservoir 22, along with packed cells exiting the separator 46.

The secondary anticoagulant line 112 and pump P5 facilitate still another step in promoting different functional characteristics in the blood fractions being separated during an automated blood component separation procedure. Compared to the previous embodiment illustrated in FIG. 6, the separation system and method illustrated in FIG. 7 permits a still further lowering of the amount of anticoagulant which must be added to the whole blood at connection 13 when the blood is withdrawn from the donor, thereby facilitating even greater platelet yields in the separator 46. Here, the anticoagulant level in the whole blood may be lowered to an amount which would be insufficient to prevent clotting in the packed cells exiting the separator 46 through tubing 56, but for the secondary anticoagulant tubing 112 and pump P5.

PRP collection procedures were conducted at a 3 percent anticoagulant level in the whole blood previously withdrawn from the donor. It is believed that reduction of the anticoagulant level to even this low level results in still further improvement in platelet yield when compared to the 4 percent anticoagulant level for example, which is itself an improvement resulting from the PRP-anticoagulant addition step illustrated in FIG. 6. The anticoagulant level of 3 percent appears to be acceptable for whole blood withdrawal during the separation procedure, in order to prevent clotting.

However, this level is insufficient for the returned packed cells exiting the separator 46. This added demand for anticoagulant may be due to the presence of white cells in the packed cells or may be due to the above described platelet activation occurring during the separation step in the separator 46. As noted previously, a significant number of platelets are returned with the packed cells, even during PRP collection procedure. The addition of secondary anticoagulant through tubing line 112 prevents such clotting. Anticoagulant is preferably added through tubing line 112 at a level sufficient to bring the anticoagulant ratio up to about four to six percent in the returned packed cells.

Thus, the primary anticoagulant pump P2 may in a preferred embodiment supply anticoagulant at a 3 percent or less level (perhaps even down to zero). The secondary anticoagulant pump P5 could supply anticoagulant at a 1 percent or more level, providing just sufficient anticoagulant to prevent clots from forming in the reinfusion circuit, but not enough anticoagulant to produce citrate toxicity in the donor.

The addition of anticoagulant to the packed cells illustrated in FIG. 7 permits the lower anticoagulant levels in blood entering the separator, for even greater platelet yield. The secondary anticoagulant addition disclosed herein and best illustrated in FIG. 7 may be employed with or without the PRP-anticoagulant addition procedure for desired PRP collection, separation and storage requirements that is disclosed herein and illustrated in FIG. 6.

While the testing for the lower acceptable limit of anticoagulant added to whole blood in an automated blood separation procedure has not yet been performed for various reasons, including questions of human efficacy and different regulatory requirements, it may be that the anticoagulant level added to the whole blood removed from the donor may be reduced to zero. Such a reduction may in fact continue to increase platelet yields from the separator 46. Because clotting typically takes several minutes, the residence time of whole blood from the needle 112 through the reservoir 22 and separator 46 may be short enough so that the first addition of anticoagulant may in fact be made through the tubing line 112 downstream of the separator, eliminating any need for anticoagulant addition at the Y-connection 13. If anticoagulant added to just-removed whole blood by pump P2 were further reduced from three percent, it is expected that the amount of anticoagulant added to the just-separated packed cells by pump P5 would need to be increased.

The ability to reduce anticoagulant levels in the whole blood and packed cells may be further facilitated by means of an improved phlebotomy needle design disclosed in the concurrently filed application of Ritchey et al entitled "Blood Component Needle Assembly for Reduced Coagulation Response" U.S. Ser. No. 538,812, assigned to the assignee of the present invention. The improved needle design resists clotting in and adjacent to the needle better than prior art needle designs.

In order to provide a complete description, a review of the second stage of the set 10, 106 will now be provided.

After the donor has been disconnected from the set 10, 106 and after the anticoagulant addition procedure set forth in FIG. 6, if utilized, the first stage portion of the set 10 is removed from the instrument H by the operator.

The platelet-rich plasma line 58 is then heat-sealed just above the inlet port to container 60. The first stage portion may then be cut away above the seal and discarded. The second stage portion B, including container 60 with the platelet-rich plasma therein, is then applied to instrument H, as illustrated in FIG. 3. It will be appreciated that in the preferred embodiment, the same particular instrument H may be used to generate PPP and platelet concentrate with set portion B as is used to generate the PRP using set portion A, although it will be recognized that this separate operation to produce the platelet concentrate may be performed on a separate instrument. Alternatively, a machine may be utilized in which set portions A and B are installed at the same time, and for example in which two needles are used (B¹), for continuous draw and continuous reinfusion to the donor.

The container 60, the platelet-poor plasma container 74 and the platelet concentrate container 78 are hung from hooks conveniently disposed along the underside of the instrument. Separator 62 is disposed on mounting 88 and its upper end is disposed in mounting cup 90 for magnetic coupling with the drive motor of the instrument. Tubing 72 interconnecting the platelet-rich plasma container 60 and the separator 62 is disposed in pump P1 and the ultrasonic air detector 86. Tubing 76 is disposed in pump P3, while tubing 80 is disposed in the hemoglobin detector 84 and clamp C1.

To produce platelet concentrate, the microprocessor controls the instrument to actuate pump P1 to pump platelet-rich plasma from container 60 into separator 62. The rotary membrane filter of separator 62 causes the platelet-rich plasma to separate into platelet-poor plasma and platelet concentrate. The platelet-poor plasma is pumped by the pump P3 from the separator 62 via line 76 for collection in the container 74. The desired platelet concentrate flows from the separator 62 via line 80 through the hemoglobin detector 84 into platelet concentrate container 78.

The instrument is programmed such that it knows the weight of the platelet-rich plasma collected in the container 60 during the first stage. Additionally, the operator may input the instrument with the desired quantity of platelet concentrate. The pumps are controlled by the microprocessor such that the desired quantity of product is provided in the platelet concentrate collection container 78. The end of the procedure is determined when the ultrasonic air detector 86 senses air in the tube 72, thereby terminating the end of the platelet concentration cycle using the second stage of the set 10, 106. If the final weight of the platelet concentrate suspension is low, the instrument can pump platelet-poor plasma from container 74 back through the device 62 and into the platelet concentrate container 78. If the final weight of the platelet concentrate suspension is high, the instrument can pump more platelet concentrate from container 78 back through separator 62 into the platelet-rich plasma container 60 and then reprocess the fluid in container 60 using the procedure set forth above.

Significantly, the platelets separated by separation device 62 require no incubation period or resuspension procedure to produce infusible platelets. This greatly reduces labor and improves the quality of the product.

In accordance with the present disclosure, it will be appreciated that improved apparatus and methods have been provided for adding anticoagulant at different stages of an automated blood component separation procedure, in order to achieve desired nutrients and pH buffering in the platelet concentrate; to lower the amount of anticoagulant added to whole blood in order to avoid citrate toxicity to the donor; to lower anticoagulant in the blood, thereby achieving greater platelet yield; to lower anticoagulant levels in packed cells returned to the donor, thereby offsetting the otherwise higher anticoagulant requirements of a platelet collection procedure, as opposed to a plasma collection procedure; and, in the set illustrated in FIG. 7, to permit still further lowering of the anticoagulant level in the whole blood for both improved donor reaction and improved platelet yield, at anticoagulant levels which, but for the set 106 and the accompanying method, would be insufficient to prevent clotting in the packed cells. It is believed that by adding anticoagulant to packed cells soon after their exit from the separator, it may in fact be possible to reduce the anticoagulant level in whole blood entering the separator to zero, which it is believed should lead to further improvements in platelet yield.

While the above disclosure has been intended to describe the preferred embodiments, it will be understood that the present invention is not limited to same, but is instead intended to include various further modifications included within the spirit and scope of the appended claims.

What is claimed is:

1. A method for increased platelet yield in an automated blood component separation procedure, the steps comprising:
   (a) providing an automated instrument for blood component separation;
   (b) providing a set including a blood component separator and means defining a flow path;
   (c) installing the set in the instrument;
   (d) separating, in the separator, the blood introduced into the set, into two or more components; and
   (e) adding anticoagulant to at least one separated component at a location in the flow path downstream of said separator;
   (f) preventing the addition of anticoagulant to whole blood at a location in the defined flow path at or upstream of the separator.

2. A method in accordance with claim 1, wherein red cell suspension is the at least one separated component to which anticoagulant is added.

3. A method of separating a red blood cell suspension from whole blood in an extracorporeal system comprising the steps of:
   transporting whole blood from a donor through an upstream flow path into an in line separator that separates a red blood cell suspension from the whole blood,
   transporting the red blood cell suspension from the separator in a downstream flow path that is also in line with the separator,
   introducing an anticoagulant solution into the upstream flow path in an amount that is sufficient to prevent clotting of the whole blood during its separation but that is not sufficient to prevent clotting of the red blood cell suspension in the downstream flow path, and
   introducing additional anticoagulant solution into the downstream flow path to prevent clotting of the red blood cell suspension after its separation from the whole blood.

4. A method according to claim 3 wherein the step of introducing anticoagulant solution into the upstream flow path comprises adding anticoagulant solution in an amount such that the anticoagulant solution level in the whole blood is less than about 8% during separation.

5. A method according to claim 4 wherein the step of introducing anticoagulant solution into the upstream flow path comprises adding anticoagulant solution in an amount such that the anticoagulant solution level in the whole blood is no more than about 6% during separation.

6. A method according to claim 4 wherein the step of introducing anticoagulant solution into the upstream flow path comprises adding anticoagulant solution in an amount such that the anticoagulant solution level in the whole blood is no more than about 4% during separation.

7. A method according to claim 4 wherein the step of introducing anticoagulant solution into the upstream flow path comprises adding anticoagulant solution in an amount such that the anticoagulant solution level in the whole blood is no more than about 3% during separation.

8. A method according to claim 4 and further including the step of returning at least a portion of the anticoagulated red blood cell suspension, together with the anticoagulant associated with it, to the donor through the downstream flow path.

9. A method according to claim 4 and further including the step of conveying at least a portion of the anticoagulated red blood cell suspension, together with the anticoagulant associated with it, to a storage container through the downstream flow path.

10. A method of separating a blood cell suspension from whole blood in an extracorporeal system comprising the steps of:
   transporting whole blood from a donor through an upstream flow path into an in line separator that separates a blood cell suspension from the whole blood,
   transporting the blood cell suspension from the separator in a downstream flow path that is also in line with the separator,
   introducing no anticoagulant solution into the upstream flow path, and
   introducing anticoagulant solution into the downstream flow path to prevent clotting of the blood cell suspension after its separation from the whole blood.

11. A method according to claim 10 and further including the step of returning at least a portion of the anticoagulated blood cell suspension, together with the anticoagulant associated with it, to the donor through the downstream flow path.

12. A method according to claim 10 and further including the step of conveying at least a portion of the anticoagulated blood cell suspension, together with the anticoagulant associated with it, to a storage container through the downstream flow path.

13. A method of separating a red blood cell suspension from whole blood in an extracorporeal system comprising the steps of:
   transporting from a donor whole blood through an upstream flow path into an in line separator that separates a red blood cell suspension from the whole blood,
   transporting the red blood cell suspension from the separator in a downstream flow path that is also in line with the separator,
   introducing no anticoagulant solution into the upstream flow path, and
   introducing anticoagulant solution into the downstream flow path to prevent clotting of the red blood cell suspension after its separation from the whole blood.

14. A method according to claim 13 and further including the step of returning at least a portion of the anticoagulated red blood cell suspension, together with the anticoagulant associated with it, to the donor through the downstream flow path.

15. A method according to claim 13 and further including the step of conveying at least a portion of the anticoagulated red blood cell suspension, together with the anticoagulant associated with it, to a storage container through the downstream flow path.

16. A method of separating blood components from whole blood in an extracorporeal system comprising the steps of:
   transporting from a donor whole blood through an upstream flow path into an in line separator that separates platelet-rich plasma and a red blood cell suspension from the whole blood,
   transporting the red blood cell suspension from the separator in a first downstream flow path that is also in line with the separator,
   transporting the platelet-rich plasma from the separator in second downstream flow path that is also in line with the separator,
   introducing an anticoagulant solution into the upstream flow path in an amount that is sufficient to prevent clotting of the whole blood during its separation but that is not sufficient to prevent clotting of either the red blood cell suspension or the platelet-rich plasma in the downstream flow paths, the yield of platelets in the platelet-rich plasma being increased by the addition of anticoagulant solution to the whole blood in an amount that is not sufficient to prevent clotting of either the red blood cell suspension or the platelet-rich plasma in the downstream flow paths, and
   introducing additional anticoagulant solution into both downstream flow paths to prevent clotting of the red blood cell suspension and the platelet-rich plasma after their separation from the whole blood.

17. A method according to claim 16 wherein the step of introducing anticoagulant solution into the upstream flow path comprises adding anticoagulant solution in an amount such that the anticoagulant solution level in the whole blood is less than about 8% during separation.

18. A method according to claim 17 wherein the step of introducing anticoagulant solution into the upstream flow path comprises adding anticoagulant solution in an amount such that the anticoagulant solution level in the whole blood is no more than about 6% during separation.

19. A method according to claim 17 wherein the step of introducing anticoagulant solution into the upstream flow path comprises adding anticoagulant solution in an amount such that the anticoagulant solution level in the whole blood is no more than about 4% during separation.

20. A method according to claim 17 wherein the step of introducing anticoagulant solution into the upstream flow path comprises adding anticoagulant solution in an amount such that the anticoagulant solution level in the whole blood is no more than about 3% during separation.

21. A method according to claim 16 and further including the step of returning at least a portion of the anticoagulated red blood cell suspension, together with the anticoagulant associated with it, to the donor through the downstream flow path.

22. A method according to claim 16
and further including the step of conveying at least a portion of the anticoagulated red blood cell suspension, together with the anticoagulant associated with it, to a storage container through the downstream flow path.

23. A method of separating blood components from whole blood in an extracorporeal system comprising the steps of:
transporting from a donor whole blood through an upstream flow path into an in line separator that separates platelet-rich plasma and a red blood cell suspension from the whole blood,
transporting the red blood cell suspension from the separator in a first downstream flow path that is also in line with the separator,
transporting the platelet-rich plasma from the separator in second downstream flow path that is also in line with the separator,
introducing no anticoagulant solution into the upstream flow path, the yield of platelets in the platelet-rich plasma being increased the addition of no anticoagulant solution to the whole blood, and
introducing an anticoagulant solution into both downstream flow paths to prevent clotting of the red blood cell suspension and the platelet-rich plasma after their separation from the whole blood.

24. A method according to claim 23
and further including the step of returning at least a portion of the anticoagulated red blood cell suspension, together with the anticoagulant associated with it, to the donor through the downstream flow path.

25. A method according to claim 23
and further including the step of conveying at least a portion of the anticoagulated red blood cell suspension, together with the anticoagulant associated with it, to a storage container through the downstream flow path.

26. An extracorporeal system for separating a red blood cell suspension from whole blood comprising:
separation means for separating a red blood cell suspension from whole blood,
means defining an upstream flow path communicating with the separation means for transporting whole blood from a donor into the separation means,
means defining a downstream flow path communicating with the separation means for transporting the red blood cell suspension from the separator,
means for introducing an anticoagulant solution into the upstream flow path in an amount that is sufficient to prevent clotting of the whole blood during its separation but that is not sufficient to prevent clotting of the red blood cell suspension in the downstream flow path, and
means for introducing additional anticoagulant solution into the downstream flow path to prevent clotting of the red blood cell suspension after its separation from the whole blood.

27. A system according to claim 26
and further including means for returning at least a portion of the anticoagulated red blood cell suspension, together with the anticoagulant associated with it, to the donor through the downstream flow path.

28. A system according to claim 26
and further including means for conveying at least a portion of the anticoagulated red blood cell suspension, together with the anticoagulant associated with it, to a storage container through the downstream flow path.

29. An extracorporeal system for separating a blood cell suspension from whole blood comprising:
separation means for separating a blood cell suspension from whole blood,
means defining an upstream flow path communicating with the separation means for transporting whole blood from a donor into the separation means,
means defining a downstream flow path communicating with the separation means for transporting the blood cell suspension from the separator,
means for preventing the introduction of an anticoagulant solution into the upstream flow path, and
means for adding an additional anticoagulant solution into the downstream flow path to prevent clotting of the blood cell suspension after its separation from the whole blood.

30. A system according to claim 29
and further including means for returning at least a portion of the anticoagulated blood cell suspension, together with the anticoagulant associated with it, to the donor through the downstream flow path.

31. A system according to claim 29
and further including means for conveying at least a portion of the anticoagulated blood cell suspension, together with the anticoagulant associated with it, to a storage container through the downstream flow path.

32. An extracorporeal system for separating a red blood cell suspension from whole blood comprising:
separation means for separating a red blood cell suspension from whole blood,
means defining an upstream flow path communicating with the separation means for transporting whole blood from a donor into the separation means,
means defining a downstream flow path communicating with the separation means for transporting the red blood cell suspension from the separator,
means for preventing the introduction of an anticoagulant solution into the upstream flow path, and
means for an adding additional anticoagulant solution into the downstream flow path to prevent clotting of the red blood cell suspension after its separation from the whole blood.

33. A system according to claim 32
and further including means for returning at least a portion of the anticoagulated red blood cell suspension, together with the anticoagulant associated with it, to the donor through the downstream flow path.

34. A system according to claim 32
and further including means for conveying at least a portion of the anticogulated red blood cell suspension, together with the anticoagulant associated with it, to a storage container through the downstream flow path.

35. An extracorporeal system for separating blood components from whole blood comprising:
separation means for separating platelet-rich plasma and a red blood cell suspension from whole blood, means defining an upstream flow path communicating with the separation means for transporting whole blood from a donor into the separation means, means defining a first downstream flow path communicating with the separation means for transporting the red blood cell suspension from the separation means, means defining a second downstream flow path communicating with the separation means for transporting the platelet-rich plasma from the separation means, means for introducing an anticoagulant solution into the upstream flow path in an amount that is sufficient to prevent clotting of the whole blood during its separation but that is not sufficient to prevent clotting of either the red blood cell suspension or the platelet-rich plasma in the downstream flow paths, and means for introducing additional anticoagulant solution into both first and second downstream flow paths to prevent clotting of the red blood cell suspension and the platelet-rich plasma after their separation from the whole blood.

36. A system according to claim 35
and further including means for returning at least a portion of the anticoagulated red blood cell suspension, together with the anticoagulant associated with it, to the donor through the downstream flow path.

37. A system according to claim 35
and further including means for conveying at least a portion of the anticoagulated red blood cell suspension, together with the anticoagulant associated with it, to a storage container through the downstream flow path.

38. An extracorporeal system for separating blood components from whole blood comprising:

separation means for separating platelet-rich plasma and a red blood cell suspension from whole blood, means defining an upstream flow path communicating with the separation means for transporting whole blood from a donor into the separation means, means defining a first downstream flow path communicating with the separation means for transporting the red blood cell suspension from the separation means, means defining a second downstream flow path communicating with the separation means for transporting the platelet-rich plasma from the separation means, means for preventing the introduction of anticoagulant solution into the upstream flow path, and means for introducing anticoagulant solution into both first and second downstream flow paths to prevent clotting of the red blood cell suspension and the platelet-rich plasma after their separation from the whole blood.

39. A system according to claim 38
and further including means for returning at least a portion of the anticoagulated red blood cell suspension, together with the anticoagulant associated with it, to the donor through the downstream flow path.

40. A system according to claim 38
and further including means for conveying at least a portion of the anticoagulated red blood cell suspension, together with the anticoagulant associated with it, to a storage container through the downstream flow path.

* * * * *